United States Patent [19]
Caillouette

[11] Patent Number: 5,827,200
[45] Date of Patent: Oct. 27, 1998

[54] METHOD AND APPARATUS FOR DETECTING AMINE PRODUCING ORGANISMS IN THE VAGINA

[76] Inventor: James C. Caillouette, 685 Oak Knoll Cir., Pasadena, Calif. 91106

[21] Appl. No.: 789,484

[22] Filed: Jan. 27, 1997

[51] Int. Cl.[6] .................................................... A61B 5/00
[52] U.S. Cl. .......................................... 600/584; 600/572
[58] Field of Search .................................. 600/573, 584, 600/562, 569, 572

[56] References Cited

U.S. PATENT DOCUMENTS

| | | |
|---|---|---|
| 2,664,879 | 1/1954 | Hardy . |
| 2,945,491 | 7/1960 | Gibbs . |
| 3,037,496 | 6/1962 | Melges . |
| 3,117,569 | 1/1964 | Wegner . |
| 3,319,621 | 5/1967 | Schwerin . |
| 3,450,129 | 6/1969 | Avery et al. ............................. 600/572 |
| 3,507,269 | 4/1970 | Berry . |
| 3,509,872 | 5/1970 | Truhan . |
| 4,311,792 | 1/1982 | Avery ...................................... 600/572 |
| 4,820,259 | 4/1989 | Stevens ........................................ 604/2 |
| 4,862,899 | 9/1989 | Bucaro .................................... 128/749 |
| 4,903,708 | 2/1990 | Saint-Amand .......................... 600/572 |
| 5,063,930 | 11/1991 | Nucci ..................................... 128/632 |
| 5,078,968 | 1/1992 | Nason .................................... 600/584 |
| 5,147,288 | 9/1992 | Schiavo ...................................... 604/1 |
| 5,425,377 | 6/1995 | Caillouette .............................. 600/572 |

OTHER PUBLICATIONS

"Vulvovaginitis", vol. 1, Chapter 37, Ronald M. Meltzer, 1994.

Urinary Incontienence and Related Urogenital Symptoms In Elderly Women: Ulla Molander, Scandinavian Association of Obstericians and Gynecologists, Supplement 158, vol. 72, 1993.

"Estrogen Deprivation and Vaginal Function In Postmenopausal Women", James P. Semmens, MD, Gorm Wagner, M.D., 1982.

Peter Smith, Dept. of Obstetrics & Gynecology, University Hospital, S–751 85 Uppsala, Sweden "Estrogens and the Urogential Tract", 1993.

Gloria Bachmann, Maturitas 22 Suppl. (1995) S21–S29 "The Estradiol Vaginal Ring—A Study of Existing Clinical Data".

Primary Examiner—Max Hindenburg
Attorney, Agent, or Firm—William W. Haefliger

[57] ABSTRACT

In the method of detecting pathogenic bacteria in the vagina, the steps that include providing an elongated assembly including an elongated carrier and a flexible outer container supported on the carrier; providing a vaginal moisture absorbing or porous material swab at one end of the assembly to communicate with the interior of the outer container; providing a frangible inner container protectively located within the outer container, and providing a flowable aqueous alkaline fluid reactant within the inner container, bending or exerting pressure on the outer container sufficient to rupture the inner container; thereby releasing reactant into the interior of the outer container to enable reactant fluid flow to the swab or porous material, for reaction with bacteria containing vaginal moisture absorbed into the swab or porous material, whereby a gaseous product of the reaction may be detected, by characteristic odor. The outer container may be defined in whole or in part by the porous material which may be woven.

36 Claims, 4 Drawing Sheets

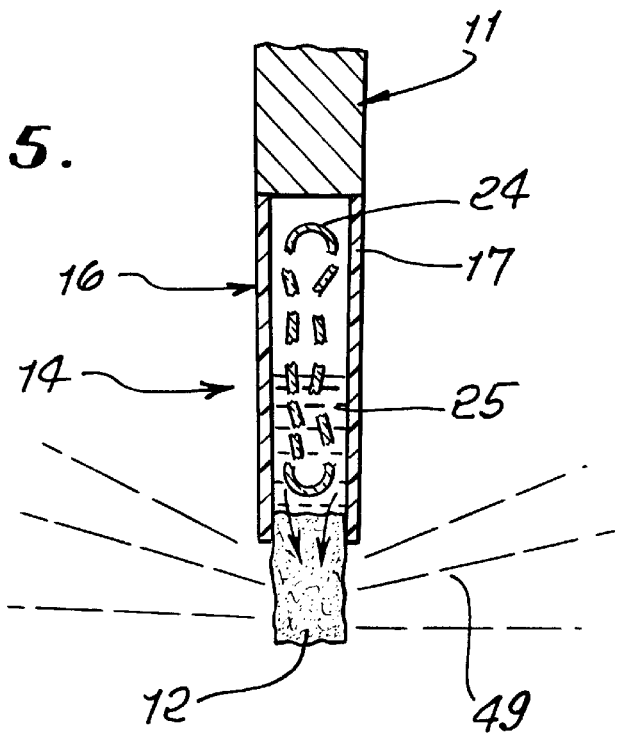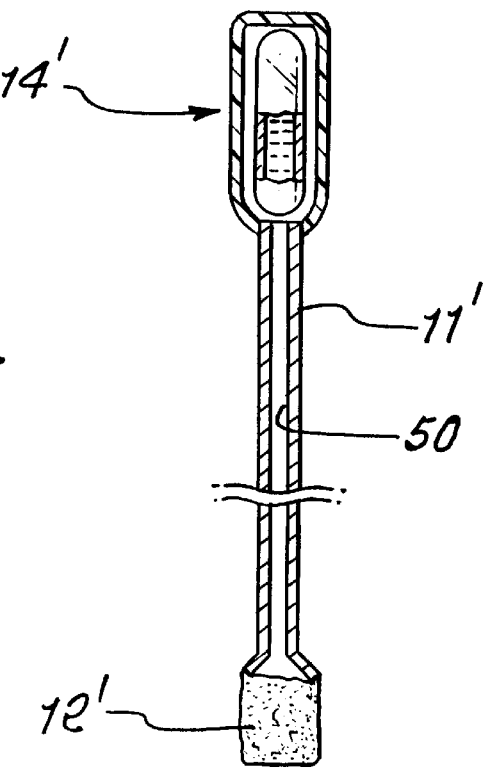

METHOD AND APPARATUS FOR DETECTING AMINE PRODUCING ORGANISMS IN THE VAGINA

BACKGROUND OF THE INVENTION

This invention relates generally to detection of bacteria in moisture, and more particularly to method and apparatus for easily and quickly testing for the presence of bacteria in moisture samples from the vagina.

There is need for simple, easily used apparatus for reliably and quickly obtaining indications of bacteria, as for example pathogenic bacteria, in moisture samples, for example which are obtainable from the vagina. There is also need for simple, effective methods to obtain such indications. Prior apparatus and techniques were cumbersome, and lacked the unusual advantages disclosed herein.

SUMMARY OF THE INVENTION

It is a major object of the invention to provide improvements in method and apparatus meeting the above needs. Basically, the method of the invention includes the following steps:

a) providing an elongated assembly including an elongated carrier and a flexible outer container supported on the carrier, b) providing a vaginal moisture absorbing swab at one end of the assembly to communicate with the interior of the outer container, c) providing a frangible inner container protectively located within the outer container, and providing a flowable aqueous alkaline fluid reactant within the inner container, d) and exerting pressure on the outer container sufficient to rupture the inner container, thereby releasing the reactant into the interior of the outer container to enable reactant fluid flow to the swab, for reaction with bacteria containing vaginal moisture absorbed into the swab, e) whereby a gaseous product of the reaction may be detected, by characteristic odor.

As will be seen, the aqueous alkaline fluid reactant stored within the inner container may advantageously consist of a dilute aqueous alkaline solution such as potassium hydroxide, as for example a 10% to 20% solution.

Another object comprises providing the outer container in close association with the swab, such as between the end of a carrier stick and the swab itself, whereby the reactant fluid when released into the outer container interior is directly accessible to the swab and to the bacteria carrying moisture sample. Alternatively, the outer container may be provided on the carrier at a location relatively remote from the swab. In that event a duct may be provided to be associated with the carrier to convey fluid reactant from the container interior to the swab. Controllable manual pressure on the outer container, after breakage of the inner container, controls flow of the reactant fluid to the swab.

Yet another object is to employ bending or manual pressure exertion on the outer container to flex its wall or walls for pressurizing the inner container to break its wall. The outer container may consist of plastic, and the inner container of thin walled glass, i.e. it is frangible.

Yet another step is to manipulate the assembly to cause the outer container to exert endwise and sidewise force on the swab to cause the swab to absorb vaginal moisture, in the vagina.

An additional object is to provide pH detection means for detection of vaginal moisture pH in conjunction with performing the steps of claim 1. That detection means may be provided on the carrier, remotely from the swab, whereby the carrier may be manipulated to contact vaginal moisture for rapid pH determination as a part of the use of the assembly as described above. Such pH determination provides an initial indication of possible presence of problematic bacteria level or levels, in vaginal moisture.

An additional object includes provision of a method of detecting pathogenic bacteria in the vagina, the steps that include a) providing an elongated assembly including an elongated carrier and a flexible outer container supported on the carrier, b) said outer container having porous means associated therewith, to communicate with the interior of the outer container, c) providing a frangible inner container protectively located within the outer container, and providing a flowable aqueous alkaline fluid reactant within the inner container, d) exerting pressure on the outer container sufficient to rupture the inner container, thereby releasing said reactant into the interior of the outer container to enable reactant fluid absorption into the interior of the outer container to enable reactant fluid flow to said porous means with bacteria containing vaginal moisture absorbed into the porous means, e) whereby a gaseous product of said reaction may be detected, by characteristic odor.

As will be seen, the porous means may be defined by the outer container; and the porous means may consist of woven material defining the outer container. This enables enhancement of contact of vaginal moisture with the reactant released from the inner container, by squeezing of the outer container to effect moisture displacement toward the reactant fluid.

These and other objects and advantages of the invention, as well as the details of an illustrative embodiment, will be more fully understood from the following specification and drawings, in which:

DRAWING DESCRIPTION

FIG. 5 is a view like FIG. 4, the liquid having flowed from the interior of the outer container to a swab at the end of the assembly, for mixing with vaginal moisture in the swab;

FIG. 6 is a view like FIG. 2, showing a modification;

DETAILED DESCRIPTION

Figure 1:
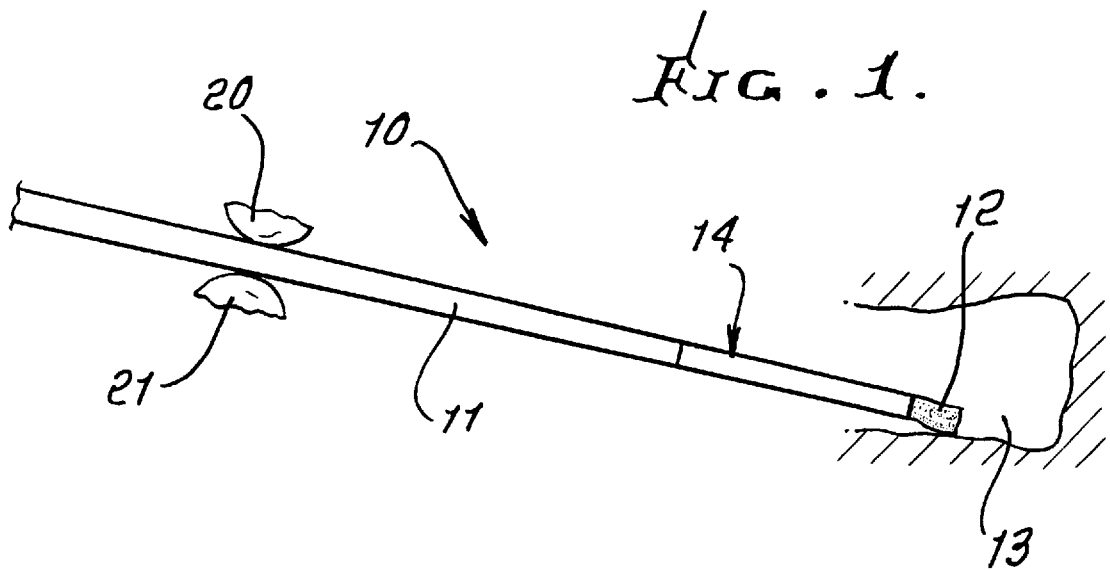
FIG. 1 is a view showing use of an elongated assembly incorporating the invention.

In FIG. 1 an elongated assembly 10 is shown to include an elongated carrier 11 such as a stick, and a swab 12 as for example a sponge, or other porous material, at the forward end of the assembly. The swab is used to absorb moisture from the vaginal cavity 13, during use of the assembly. FIG. 1 shows a user's finger and thumb 20 and 21 manipulating the assembly.

Controllable test liquid supply means is provided at 14, between the forward end of the carrier 11 and the swab 12. The means 14 is adapted to be manually squeezed to effect controllable communication of contained test liquid to the swab 12, for reaction with vaginal moisture picked up by the swab. Since the supply means or unit 14 is located between 11 and 12, it provides a test means incorporated in or on the assembly 10.

Figure 2:
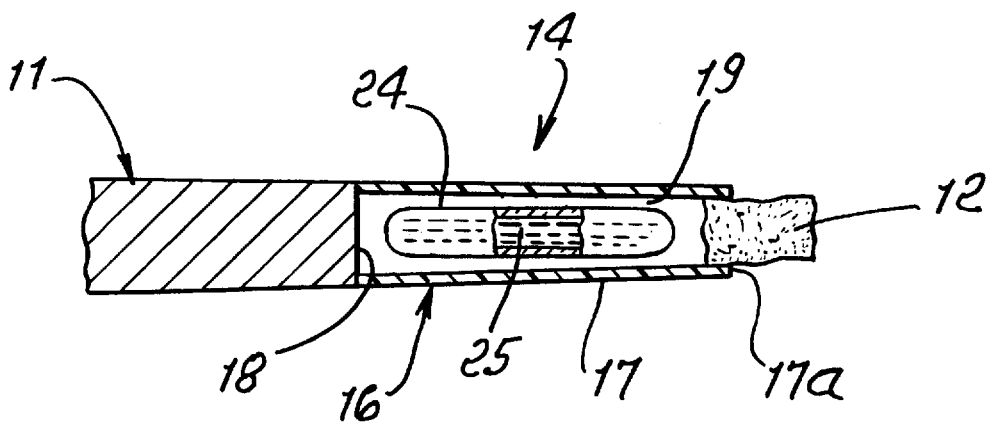
FIG. 2 is an enlarged section taken lengthwise through an end portion of the FIG. 1 assembly.

FIG. 2 shows the means or unit as incorporating an outer container 16 which is elongated and tubular, having cylindrical side wall 17, and end wall 18 attached to the forward end of carrier 11. The interior 19 of the container communicates with swab 12, and for this purpose the swab may be received into the open forward end portion 17a of the outer container, thereby mounting the swab to the container.

Figure 3:
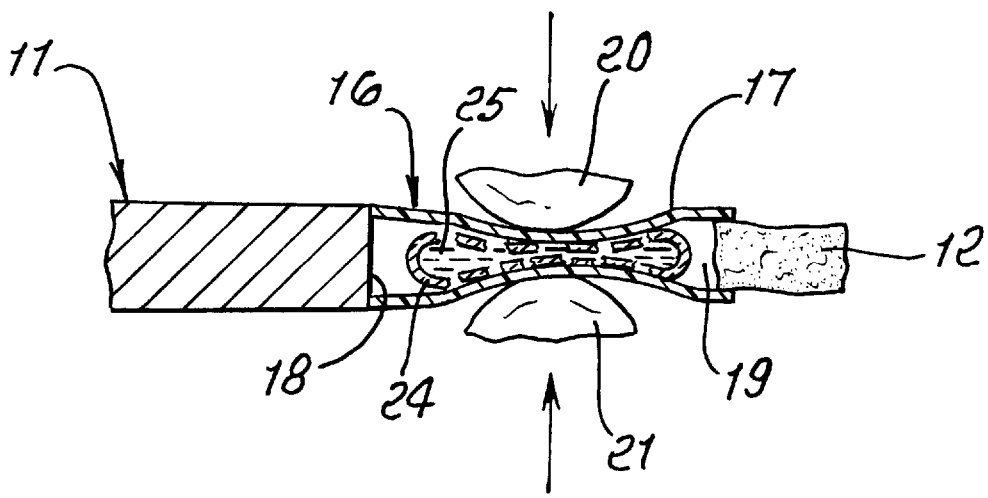
FIG. 3 is a view like FIG. 2, showing manual fracture or rupture of an inner container located within an outer container, as also seen in FIG. 2.
Figure 4:
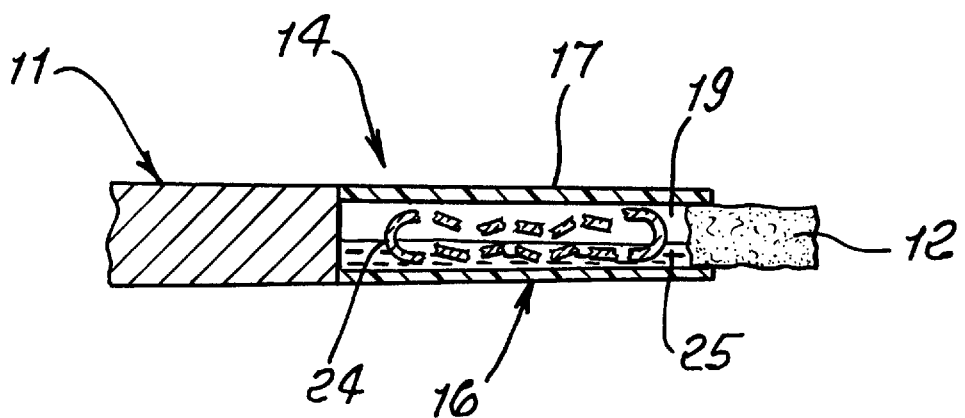
FIG. 4 is a view like FIG. 3, showing liquid from the inner container having been released into the interior of the outer container.

A frangible inner container 24 is located within the interior 19 of container 16, and may be elongated, as shown. Container 24 may consist of a hollow, thin-walled glass capsule to contain test liquid 25. The outer container side wall 17 may consist of relatively stiff plastic material, which is sufficiently flexible to be bent or squeezed, as by or between user's finger and thumb 20 and 21, as seen in FIG. 3. Such bending or squeezing, exerting pressure on the outer container, is sufficient to rupture the inner container as seen in FIG. 3, thereby releasing contained reactant test liquid 25 into the interior 19 of the outer container. See FIG. 4. This provides for controlled access of the test liquid to the swab, for reaction with the vaginal moisture, as seen in FIG. 5. See orientation of the assembly 10 to cause gravitation of the test liquid to flow into contact with the end of the swab carried by the forward end portion of the outer container.

In one form of the invention, the test liquid consists of dilute aqueous alkaline liquid for reaction, as with bacteria in the vaginal moisture in the swab. Such bacteria may be pathogenic. One example of the alkaline test liquid is a 10% to 20% aqueous solution of potassium hydroxide. When such solution contacts amines resulting from bacterial activity, a characteristic odor is produced, as by formation of gaseous amines such as cadaverine and/or putrescine indicated at 49. The user may thereby quickly and efficiently determine the existence of bacteria such as pathogenic bacteria in the vaginal moisture, using a simple unitary test means and procedure as described.

FIG. 6 shows a modification in which the test liquid supply means 14' is like 14, but located and supported at the opposite end of the carrier 11'. A duct 50 is provided in the carrier to communicate the released liquid to the swab 12'. The user can manipulate the stick and swab, and also control test liquid delivery to the swab, from the remote or external end of the carrier. Note the reduced diameter of the carrier.

Figure 7:
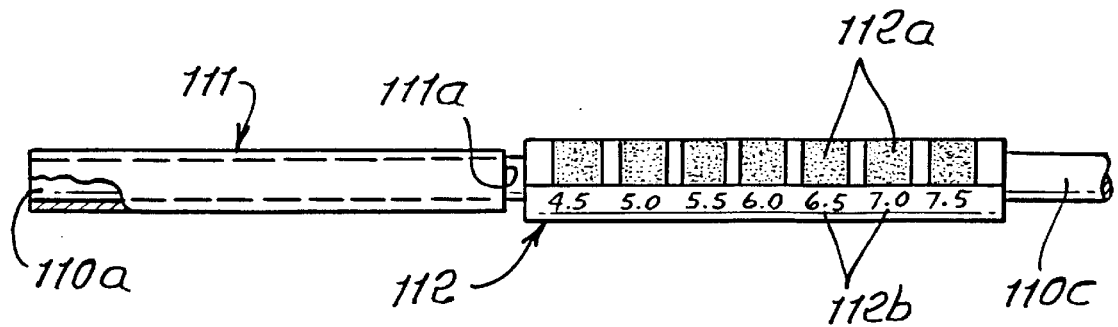
FIG. 7 is an enlarged view of a ph detection means on a carrier, such as is also shown in FIG. 1.

FIG. 7 shows provision of a pH detection means as described in my U.S. Pat. Nos. 5,577,512; 5,425,377; and pending application Ser. No. 08/699,251 incorporated herein by reference.

As shown, a first means 111 may comprise a pH indication strip, such as a Nitrazine® Phenaphthazine strip, wound about the stick or carrier end portion 110a and adhered to same as by an adhesive. A color comparison pH measurement means 112 may comprise a thin paper strip adhered to the stick surface to extend lengthwise of the stick from the edge or end 111a of the first means 11. A second means is shown to have color gradations in a series sequence, as in colored bands 112a positioned lengthwise of or along the stick. In addition, the paper strip 112 may include pH numerical indicators 112b along side the color gradation bands, to enable:

visual color comparison of the pH indication means 111 (immediately after its exposure to o vaginal fluid) with the bands 112a, for visual selection of that band most close in color to the color of the indication means 111; and immediate visual readout of the pH number adjacent the selected band.

The stick projects freely at 110c away from the first and second means 111 and 112 for manual manipulation to first obtain pH indication of vaginal moisture at one end of the stick, and to enable visual interpretation of that indication by color comparison with the second means, without manual release of the stick. The stick or carrier is then used to obtain a test for bacteria presence in vaginal fluid, as described above. The stick is then disposable, or may be disposed of, after a swabbing step to be described.

Figure 8:
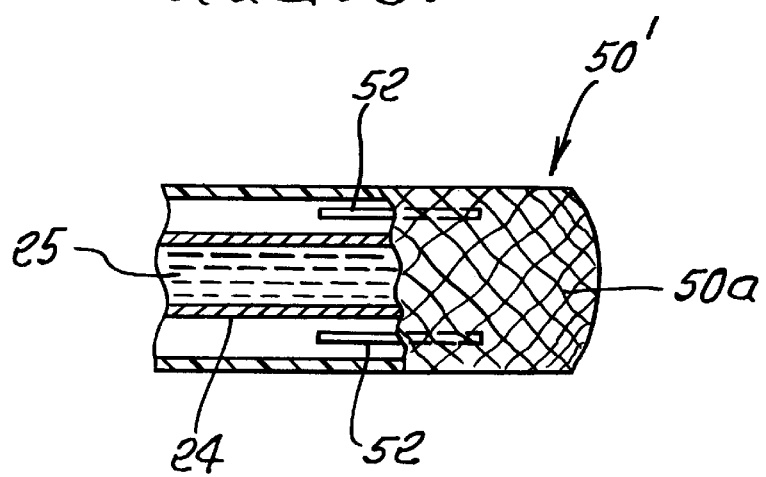
FIG. 8 is a side view showing a modification.

FIG. 8 shows another form of the invention, elements of which correspond to elements of FIGS. 1–7 bearing the same identifying numerals.

In FIG. 8, the outer container has porous means associated therewith, to communicate with the interior of the outer container. The provision of such porous means enables reactant flow of reactant fluid directly released from the fractured inner container into the porous means for reaction with vaginal moisture absorbed into the porous means. Accordingly, flow of reactant fluid to a separate area spaced endwise from the container is not required.

As shown, part or all of the outer container 50 defines an associated porous means, as in the form of a wall 50a consisting of flexible woven material located for example at the end of the assembly. The woven material may consist of synthetic or non-synthetic material, closely woven in a warp and woof pattern, and may include stiffener means associated therewith to assist in maintaining the tubular shape of the outer container. See for example stiffener elements 52.

When squeezed, the outer container deflects to transmit force to the inner container 24 to fracture its wall. This effects release of the reactant fluid into the interior 19 of the outer container and direct access of said reactant fluid to vaginal moisture absorbed into interstices formed by porous means which may be defined by the outer container or part thereof. Such squeezing of the outer container also tends to displace moisture therein toward the reactant fluid, for reaction therewith as described above. A more direct testing method is thereby provided.

The fluid capsule 24 may contain a dye of such color as to make it clear that the fluid in capsule 24 has permeated the sponge 12 or woven cover 50a, during use. Usable dyes include Methylene Blue
    USP 1% (10 mg/ml)
    NDC 0517-0373-70
Indigo Carmine
    0.8% solution
    NDC 0517-0375-10

Both dyes are approved for IM or IV use by the U.S. Food and Drug Administration.

The test liquid released from the inner container may be used to react with vaginal moisture absorbed by or on the porous means 12, for detection of estrogen level. See in this regard my pending applications Ser. No. 08/570,534, filed Dec. 11, 1995, and Ser. No. 08/699,251, filed Aug. 19, 1996, incorporated herein by reference.

I claim:

1. In the method of detecting pathogenic bacteria in the vagina, the steps that include
   a) providing an elongated assembly including an elongated carrier and a flexible outer container supported on the carrier,
   b) providing a vaginal moisture absorbing swab at one end of the assembly to communicate with the interior of said outer container,
   c) providing a frangible inner container protectively located within the outer container, and providing a flowable aqueous alkaline fluid reactant within the inner container,
   d) exerting pressure on the outer container sufficient to rupture the inner container, thereby releasing said reactant into the interior of the outer container to enable reactant fluid flow to said swab, for reaction with bacteria containing vaginal moisture absorbed into the swab,
   e) whereby a gaseous product of said reaction may be detected, by characteristic odor.

2. The method of claim 1 wherein said aqueous alkaline fluid reactant consists essentially of a dilute aqueous solution of potassium hydroxide.

3. The method of claim 2 wherein said solution consists of 10 to 20% potassium hydroxide.

4. The method of claim 1 wherein said outer container is provided in relatively close association with said swab.

5. The method of claim 1 wherein said outer container is provided at a location on the carrier that is relatively remote from the swab.

6. The method of claim 5 including providing a duct associated with the carrier to convey fluid reactant from the container interior to the swab.

7. The method of claim 1 wherein said pressure is exerted manually.

8. The method of claim 1 including manipulating said assembly to cause the outer container to exert endwise and sidewise force on the swab to cause the swab to absorb vaginal moisture, in the vagina.

9. The method of claim 1 also including providing a pH detection means for detection of vaginal moisture pH in conjunction with performing the steps of claim 1.

10. The method of claim 9 wherein said pH detection means is provided at a location on the carrier.

11. The method of claim 9 including locating said pH detection means on the carrier, relatively remotely from said swab.

12. The method of claim 9 including providing an auxiliary carrier, and locating said pH detection means on the auxiliary carrier.

13. The method of claim 7 including controlling said manual pressure to control reactant fluid flow to the swab.

14. In apparatus for detecting pathogenic bacteria in the vagina, the combination that includes:
   a) an elongated assembly including an elongated carrier and a flexible outer container supported on the carrier,
   b) a vaginal moisture absorbing swab at one end of the assembly to communicate with the interior of said outer container,
   c) a frangible inner container protectively located within the outer container, and a flowable aqueous alkaline fluid reactant within the inner container,
   d) whereby pressure exerted on the outer container sufficient to rupture the inner container thereby releases said reactant into the interior of the outer container to enable reactant fluid flow to said swab, for reaction with bacteria containing vaginal moisture absorbed into the swab,
   e) and whereby a gaseous product of said reaction may be detected, by characteristic odor.

15. The combination of claim 14 wherein said aqueous alkaline fluid reactant consists essentially of a dilute aqueous solution of potassium hydroxide.

16. The combination of claim 15 wherein said solution consists of 10 to 20% potassium hydroxide.

17. The combination of claim 14 wherein said outer container is located in relatively close association with said swab.

18. The combination of claim 14 wherein said outer container is located at a position on the carrier that is relatively remote from the swab.

19. The combination of claim 18 including a duct associated with the carrier to convey fluid reactant from the container interior to the swab.

20. The combination of claim 14 wherein said carrier is elongated for manipulating said assembly to cause the outer container to exert endwise and sidewise force on the swab to cause the swab to absorb vaginal moisture, in the vagina.

21. The combination of claim 14 also including a pH detection means on the assembly for detection of vaginal moisture pH, thereby to detect abnormal or pathogenic bacteria, or estrogen level.

22. The combination of claim 21 wherein said pH detection means is located on the carrier, relatively remotely from said swab.

23. The combination of claim 21 including an auxiliary carrier, said pH detection means located on the auxiliary carrier.

24. In the method of detecting pathogenic bacteria in the vagina, the steps that include
   a) providing an elongated assembly including an elongated carrier and a flexible outer container supported on the carrier,
   b) said outer container having porous means associated therewith, to communicate with the interior of the outer container,
   c) providing a frangible inner container protectively located within the outer container, and providing a flowable aqueous alkaline fluid reactant within the inner container,
   d) exerting pressure on the outer container sufficient to rupture the inner container, thereby releasing said reactant into the interior of the outer container to enable reactant fluid absorption into the interior of the outer container to enable reactant fluid flow to said porous means with bacteria containing vaginal moisture absorbed into the porous means,
   e) whereby a gaseous product of said reaction may be detected, by characteristic odor.

25. The method of claim 24 wherein said porous means is defined by the outer container.

26. The method of claim 24 wherein said porous means is defined by woven material.

27. The method of claim 25 wherein said porous means is defined by woven material.

28. The method of claim 24 wherein said aqueous alkaline fluid reactant consists essentially of a dilute aqueous solution of potassium hydroxide.

29. The method of claim 28 wherein said solution consists of 10 to 20% potassium hydroxide.

30. The method of claim 24 including manipulating said assembly to cause the outer container to exert endwise and sidewise force on the swab to cause the swab to absorb vaginal moisture, in the vagina.

31. The method of claim 24 also including providing a pH detection means for detection of vaginal moisture pH in conjunction with performing the steps of claim 1.

32. In the method of detecting a substance in vaginal moisture, the steps that include
   a) providing an elongated assembly including an elongated carrier and a flexible outer container supported on the carrier,
   b) providing porous means to communicate with the interior of the outer container,
   c) providing a frangible inner container protectively located within the outer container, and providing a flowable fluid reactant within the inner container,
   d) said porous means adapted to absorb vaginal moisture containing substance to be detected,
   e) exerting pressure on the outer container sufficient to rupture the inner container, thereby releasing said reactant into the interior of the outer container to enable reactant fluid access to said porous means to react with said substance enabling detection of said substance.

33. The method of claim 32 including also employing said assembly to detect estrogen level.

34. The method of claim 32 wherein said fluid reactant has a distinguishing color, visible when the reactant flows to said porous means.

35. The method of claim 34 including a dye provided in said fluid reactant, causing said reactant to exhibit said color.

36. The method of claim 35 wherein said dye is selected form the following group:
   Methylene Blue
   Indigo Carmine.

* * * * *